United States Patent
Brill et al.

(10) Patent No.: US 8,610,715 B2
(45) Date of Patent: Dec. 17, 2013

(54) IMAGE VOLUME BROWSER WITH VARIABLY ADJUSTABLE ORIENTATION MEASUREMENT

(75) Inventors: Roland Brill, Erlangen (DE); Helmut König, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 793 days.

(21) Appl. No.: 12/591,918

(22) Filed: Dec. 4, 2009

(65) Prior Publication Data

US 2010/0171741 A1 Jul. 8, 2010

(30) Foreign Application Priority Data

Jan. 7, 2009 (DE) .......................... 10 2009 004 005
Jan. 26, 2009 (DE) .......................... 10 2009 006 148

(51) Int. Cl.
G06T 17/00 (2006.01)
G06T 15/00 (2011.01)
G09G 5/00 (2006.01)

(52) U.S. Cl.
USPC ............................ 345/424; 345/419; 345/619

(58) Field of Classification Search
None
See application file for complete search history.

(56) References Cited

U.S. PATENT DOCUMENTS

| | | | |
|---|---|---|---|
| 5,986,662 A | 11/1999 | Argiro | |
| 7,061,484 B2 * | 6/2006 | Bailey et al. | 345/419 |
| 2005/0184988 A1 | 8/2005 | Chandra | |
| 2007/0118408 A1 | 5/2007 | Kariathungal | |
| 2007/0127790 A1 | 6/2007 | Barth | |
| 2007/0127792 A1 | 6/2007 | Virtue | |
| 2011/0255761 A1 * | 10/2011 | O'Dell et al. | 382/131 |

FOREIGN PATENT DOCUMENTS

DE 102006054137 A1 7/2007

* cited by examiner

*Primary Examiner* — Kee M Tung
*Assistant Examiner* — Leon T Cain, II
(74) *Attorney, Agent, or Firm* — Harness, Dickey & Pierce, P.L.C.

(57) ABSTRACT

A method, a monitor control module and system are disclosed for displaying a medical image from a volume dataset on a monitor of a computer-aided device, whereby, in addition to the image a number of orientation images from the volume dataset are to be displayed. In at least one embodiment, the user determines an orientation measurement beforehand, on the basis of which orientation images will be selected from the volume dataset and presented for display with the image. The orientation measurement can be either based on distance or be the result of an anatomic model.

17 Claims, 3 Drawing Sheets

IMAGE VOLUME BROWSER WITH VARIABLY ADJUSTABLE ORIENTATION MEASUREMENT

PRIORITY STATEMENT

The present application hereby claims priority under 35 U.S.C. §119 on German patent application numbers DE 10 2009 006 148.7 filed Jan. 26, 2009 and DE 10 2009 004 005.6 filed Jan. 7, 2009, the entire contents of each of which are hereby incorporated herein by reference.

FIELD

At least one embodiment of the invention lies in the field of medical information technology and relates in particular to the display of medical slice images from a volume dataset.

BACKGROUND

Modern imaging methods in medical technology mean that a doctor, while undertaking a diagnosis for example, is confronted by a plurality of sectional images that he must evaluate. Looking through large numbers of such sectional images is very tiring and as such is liable to errors. On the other hand very great care has to be taken during this task, since the result generally has a decisive effect on the further treatment of the patient.

The desire is accordingly to improve the display of sectional image data. In particular an orientation in a three-dimensional space and in relation to the human body is to be made easier.

In the prior art the practice of displaying additional further orientation images in addition to the image to be displayed or the sectional image on which the examiner is currently concentrating is known. Thus a method from the prior art typically aims to present three correlated views, each orthogonal to each other, which mutually serve as an overview. The orientation images also serve to make the environment of the respective image and relevant anatomic structures rapidly detectable.

Image browsers are also known in the prior art which make it possible to switch back and forth or to scroll between individual images. To obtain an overview of the anatomic structure of the image to be displayed, it is thus known that a switch can be made from the (current) image to be displayed to further images. The further images to which the user can switch are selected from a volume dataset in accordance with a rigid pre-configurable scheme. For example each adjacent fifth, tenth or fifteenth image can be retrieved for further display in relation to the (current) image, so that the user can then switch from the current image to the adjacent images. The disadvantage associated with this is that the doctor, for the purposes of better orientation, must perform a manual user interaction (which once again diverts him from his work), so that he cannot automatically obtain any combined display of the image and the further images.

Although the prior-art browsers mentioned above do offer the user a degree of assistance in orientation—they are also still associated with further disadvantages. On the one hand orientation in the overall volume dataset is only possible with difficulty, since this typically consists of hundreds of individual sectional images. In other words a very large number of sectional images must be viewed. Another disadvantage is that there is no variable adjustment available to the user, but rather the further images that are to be displayed for the current image are defined in the same way in each case. If the volume dataset for a CT examination relates for example to the entire stomach area of a patient and if only the area of the porta hepatis is of interest clinically, with the previous browsers the doctor had to view a plurality of sectional images and so-to-speak "work towards" the image with the porta hepatis. In doing so he must orient himself in the large volume of sectional images in order to arrive at the relevant area. It is easy to see that this method—especially with complex circumstances—is very liable to errors and is inefficient.

SUMMARY

In at least one embodiment of the present invention is therefore to demonstrate a way in which the orientation and the overview in the display of medical images from a volume dataset can be improved. In addition finding relevant structures in the volume dataset is to be simplified and speeded up. In particular it is to be possible explicitly to access or find an anatomic structure in the display of images from the volume dataset, so that further processes (a diagnosis or study on the part of the doctor) are less liable to errors.

At least one embodiment of the inventive method will be described below. Features, advantages or alternate embodiments are also mentioned here. In other words the physical aspects (which are typically directed to a system, a device or a product) can also be developed with the features which are described or claimed in connection with the method. The corresponding functional features of the method are embodied in such cases by corresponding physical modules, especially by hardware modules.

At least one embodiment of a method is for displaying at least one medical image from a volume dataset, whereby the image is to be displayed on a monitor of a computer-aided device and whereby in addition to the image, a number of orientation images from the volume dataset of the image are to be displayed, comprising:

Determination of an orientation measurement or provision of a predetermined orientation measurement;

Application to the volume dataset of the orientation measurement determined or provided, in order to select from the volume dataset the orientation images which correspond to the orientation measurement determined or provided;

Display of the image together with the selected orientation images.

The technical terms used within the framework of embodiments of this invention will be explained in greater detail below.

The term "display" relates to a display of datasets especially image datasets, on a screen or monitor. The display can relate to the entire monitor but also to only a part of the monitor, and is typically directed for example to display in a window. The image is displayed on a monitor of the computer-aided device.

The computer-aided device can involve a medical workstation, a desktop computer, a portable computer or other mobile devices (PDAs etc.). The device can involve an operating console of imaging apparatus (CT, MRT, ultrasound etc.).

At least one embodiment of the invention makes a distinction between the terms image, orientation images and navigation images. The term image relates to the current image or image to be displayed which is of central interest to the examiner. The orientation images provide the examiner with an orientation aid and comprise information about the spatial position of the respective image within the volume dataset. As a rule a number of orientation images are displayed for the image. In exceptional conditions it may however also be possible to display only a single orientation image, as a comparison image so to speak.

The orientation images always have a relationship to the image (to be displayed), since they are intended as an overview and possibly additionally as an orientation aid for the respective image. In other words there is an assignment between image and respective orientation images so that, on a switch from a first image to a second image, a switch is also made between the respective orientation images (for example from a first set of orientation images to a second set of orientation images).

The navigation image is an overview display and is used for improved navigation between the individual images and for improved orientation. The navigation image can be displayed automatically or if necessary in response to a signal as an additional aid to the examiner in order to show an overview display of the three-dimensional volume dataset recorded. In accordance with the preferred embodiment the navigation image is provided with position markings for the respective orientation images and/or with position markings for the image. The navigation image can be two-dimensional or three-dimensional. Usually the navigation image is a reconstruction image orthogonal to the image and/or to the orientation images.

The orientation measurement involves a function which is applied to the three-dimensional volume dataset in order to segment or classify the latter into specific areas or sections. The orientation measurement is a selection scheme and is designed to be used as a basis for a (user)-configurable selection of orientation images from the volume dataset as an orientation overview. The display of the orientation images in addition to the image enables an improved orientation to be achieved.

In accordance with an example embodiment of the invention two different measures of orientation are provided. The orientation measurement can thus firstly involve a distance-related orientation measurement, with the spacing of the orientation measurement identifying the distance of the respective orientation image from the image (to be displayed). In addition the orientation measurement can secondly also be anatomy related. The anatomy-related orientation measurement is based on an anatomic model which makes it possible to explicitly find relevant anatomic structures in the image stack.

To this end all or selected slices of the volume dataset are assigned an anatomic code from a controlled medical vocabulary. For example all organic structures which belong to the liver are identified by the code "liver" and all anatomic structures which belong to the pancreas are identified by the code "pancreas". The relevant anatomic structures are selected on the basis of the anatomic model. In order to do this, the anatomic model takes into account metadata relating to the examination and/or the patient. In particular the anatomic model takes account of the anatomic size conditions, depending on height, weight, age, gender and further metadata in relation to the patient. In addition the clinical problem and the type of examination (CT, MRT, US etc.) can be taken into account.

In accordance with an example embodiment of the present invention a user interface is provided via which the user can set particular parameters beforehand for the display. Cumulatively or alternately a further interface can be embodied (or the existing interface can be expanded accordingly) via which the further parameters can be set which can be derived from a workflow context within the framework of which the image is to be displayed. This has the advantage of enabling support which is as automated as possible to be provided, with for example parameters for the display of the images being able to be derived automatically for the display with the selected orientation images from the higher ranking workflow.

In particular he can specify here the anatomic structures that he regards as relevant and that are therefore to be taken into account in the anatomic model. For example he can select here that only one choice of anatomic structures is to be displayed. The anatomic model is then applied to the volume dataset to select the orientation images for the image and display them. Preferably on the basis of the anatomic model (which takes account of metainformation, a distance of the relevant structures from the image is calculated. Then all those sectional images from the 3D dataset are determined that are at the calculated distance from the image and these will be displayed as orientation images for the image.

In accordance with an example embodiment of the present invention the distance for the distance-based orientation measurement can be set to increase. In other words a configurable growth parameter can be taken into account that indicates with which factor or growth parameter the distance from the orientation images to be displayed grows in relation to the image. The growth parameter is preferably preset or is derived from the context (workflow).

Alternately it can also be entered manually by the user. Preferably it is preset here that the orientation images that are located close to the image are displayed with a smaller distance and the orientation images which are located further away from the image are displayed with a greater distance. The result of this is that the core area of interest, which, although it lies on the image with relatively many neighboring images, is shown in great detail and that the number of orientation images decreases all the more, the further away one is from the current image. The advantage of this is that the user is only given the relevant information and is not confronted with a plurality of unnecessary slices. In an alternate embodiment the distance between the respective orientation images can however also be selected as constant or it can also be determined manually by a corresponding interface and a user input.

In a further variant the distance between the orientation images is also able to be configured for the anatomy-related orientation measurement.

In accordance with a further embodiment of the present invention, in addition to the display of the image with the orientation images, a navigation image is also displayed. In this case it is possible to select the times at which the different images are displayed. On the one hand it is possible for all orientation images to be displayed at the same time as the image. Alternatively orientation images can be displayed only after a period of time or in response to a user action. Likewise the navigation image can be displayed at the same time as or in parallel to the display of the image and/or the display of the orientation images. Alternatively the navigation image can also be displayed offset in time at a later time, for example initiated by a user interaction (e.g. a corresponding confirmation signal).

According to an example embodiment the inventive system includes a user interface which makes it possible to determine display parameters. The display parameters are use for configuration of the display of the image, of the orientation images and/or of the navigation image. In such cases different display parameters can also be defined for image, orientation images and navigation image. The display parameters typically involve the size of the display, the position of the display on the monitor, the resolution of the images, contrast parameters, the time of the display, the thickness of the display, if a number of sectional images are to be displayed for display superimposed as a 3D image stack with a specific thickness.

In accordance with a further advantageous embodiment of the invention the navigation image is interactive. In other words a corresponding display or a change to the display can be achieved via corresponding signals of the user within the navigation image. It is thus possible for the user to use the navigation image interactively to navigate in the volume dataset. If for example he chooses a specific image or a specific range in the navigation image, this automatically leads to the assigned image with its orientation images being loaded and displayed. In this case it is possible for the user to select a sectional image in the navigation image so that the corresponding image with its orientation images will be loaded. Likewise it is also possible for the user to activate a range within the navigation image. This leads to all images with respective orientation images being displayed that are assigned to this range.

In accordance with an advantageous development of at least one embodiment of the present invention there is provision for the navigation image to be three-dimensional and for simplified use for an anatomic structure to also be able to be incorporated or stored in the three-dimensional display. This makes it possible for the user immediately and so to speak at a glance to recognize the underlying anatomic structure in each case. Overall this also leads to a marked reduction in errors in the subsequent diagnosis or study of the image material. In accordance with a simple alternate embodiment the navigation image is merely two-dimensional. Here too an anatomic structure—as a two-dimensional image—can be shown.

As already mentioned, the display of the image with its orientation images and the display of the navigation image occur at the same time. This has the advantage of the user having all the necessary information to hand immediately and directly and not having to make any further separate user entries. As an additional orientation aid the image includes a reference to its position in the navigation image. In addition it is also possible for all orientation images for the image to be identified by such references, so that the position of the respective orientation images within the volume dataset is also indicated. Preferably this can be performed with a reference e.g. with arrows in a graphical display or with other assignment references.

So that the method is able to be adapted in the optimum possible way to the respective application there is provision, as well as the display parameters, for further factors to also be able to be taken into account in order to configure the display. The factors in this case can be obtained automatically by the system, can be preset or can be set by the user. Thus it can be set for example that initially a first number of orientation images are displayed for the image and that in a later phase another, as a rule smaller number of orientation images is displayed for the image. This has the advantage that the number of relevant images can be reduced within the framework of the ongoing inspection process, since as a rule the focus can be set more narrowly as the display proceeds.

A further significant aspect of an embodiment of the present invention is also to be seen in the fact that the method is able to be integrated into a medical workflow so that, depending on the alignment of the medical workflow, the display process can be specifically tailored. For this purpose automatic default settings are made for displaying the image along with the orientation images and where necessary the navigation image. These defaults are based on metainformation comprising: The type of examination and the clinical problem. If for example the clinical problem relates to the clarification of an icterus (jaundice) and a computed tomographic image of the abdomen has been created, it can be automatically derived from this metainformation that for example the porta hepatis and the pancreas head are of outstanding significance and should also be displayed.

The automatic configuring of the inventive display process on the basis of context information (metainformation) is undertaken by accessing a rule base in which medical knowledge is stored. Knowledge from guidelines can also be stored in the rule base.

The image to be displayed can either be displayed as a two-dimensional sectional image or as a three-dimensional image. If the image is to be displayed as a three-dimensional image, a so-called multi planar reformatting is executed. In other words a number of sectional images from the volume dataset are calculated in combination and are to be displayed as a combined three-dimensional overall image. For this the respective origin images are superimposed and a three-dimensional overall image is computed.

This method is especially suitable for recognizing specific three-dimensional structures within the volume dataset, since specific structures can be more easily recognized in a three-dimensional display than in a two-dimensional display or than in a sequence of two-dimensional displays. Thus if the image to be displayed is three-dimensional in this embodiment the defaults can be selected for how many slices are to be included for display. Optionally the orientation images can then be two-dimensional or three-dimensional. Usually three-dimensional orientation images will also be displayed for a three-dimensional image.

However it is possible to configure how many slices are included for the display of the orientation images. In particular the thickness of the image can be set differently and separately from the thickness of the orientation images. Usually the slice thickness increases with the distance from the image (to be displayed). In other words the display in the center around the image to be displayed is very detailed and becomes ever coarser as the distance from this center increases.

A further solution to the problem is provided in a monitor control model for controlling the display of the medical image on the monitor.

A system is also disclosed for displaying at least one image from the volume dataset.

A computer program product and a storage medium are also disclosed, that are embodied for executing the method described above when the program is executed on a computer.

With at least one embodiment of the inventive solution, a series of advantages can be achieved. Thus it is significantly easier for the examiner to provide himself with an overview of the overall situation. In addition he can find the relevant images for a clinical problem much more quickly without being unnecessarily diverted by a flood of image datasets. In addition orientation is made easier by orientation images being displayed from the surroundings of the respective image along with each image. This means that the danger can be greatly reduced of inadvertently overlooking relevant structures. In addition the navigation in the volume dataset is significantly simplified since the respective image positions in the navigation image are able to be detected at a glance. In addition specific anatomic structures can be looked for quite explicitly. This is especially possible through the application of the anatomy-related orientation measurement which makes it possible to enter specific anatomic structures (e.g.

liver, kidneys, stomach) so that exactly the structures entered are taken into account in the display.

BRIEF DESCRIPTION OF THE DRAWINGS

In the detailed description of the figures given below example embodiments, which are not to be understood as being restrictive, will be discussed with their features and further advantages with reference to the drawing. The figures are as follows.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The basic principle of at least one embodiment of the present invention will be described below.

As part of a medical task a doctor would like to view image material. To this end an image B is loaded onto a monitor M of a computer-aided system. Since the image datasets as a rule have a very high volume of data it is necessary for the doctor to know his way around within the plurality of the slices displayed of be able to orient himself and navigate within them.

This work is very tiring since the doctor is confronted with a plurality of image contents which in some cases only differ from each other marginally, so that a very attentive and specific viewing is required. In addition an orientation based on the type of examination (e.g. CT, MRT etc.) is in some cases only possible with great difficulty and as a rule the doctor needs a degree of expert and empirical knowledge to be able to recognize the anatomic structure to which the respective slice belongs.

This is the starting point of an embodiment of the present invention. Inventively not only the current image B to be displayed will be displayed. Inventively there is provision that, as well as the current image B, further image contents will also be displayed for improved orientation on the monitor M.

In accordance with a first embodiment there is provision that, in addition to the image B, orientation images OB will also be displayed on the monitor M. The orientation images OB involve images adjacent to or surrounding the image. If the image B changes, the orientation images OB displayed also change. As well as the current image B on which the focus of observation of the examiner lies, a selection of ambient images arranged before and/or afterwards in relation to the image B will also be displayed. Preferably the orientation images OB can be displayed as the distance from the image B increases. The advantage of this is that in the immediate vicinity of the image B to be observed, which lies in the focus of the interest, a more detailed display can be achieved, while it becomes ever coarser as the distance from the image B increases.

Figure 1:
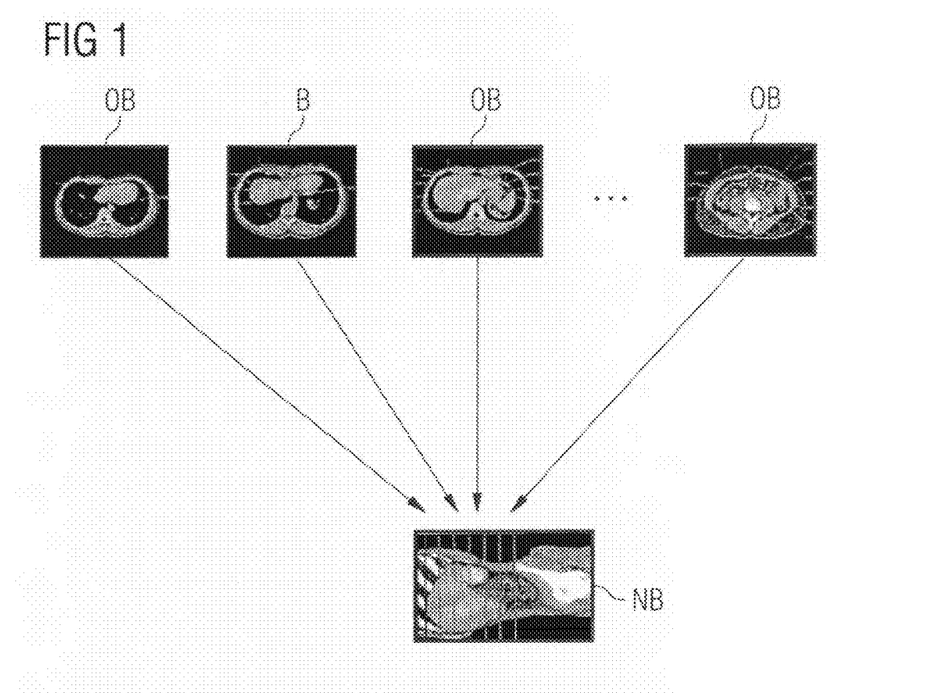
FIG. 1 shows an overview-type diagram of orientation images with constant spacing, an image and a navigation image which refers to an example.

As an alternative it is possible to display orientation images OB with a constant distance from image B. This is shown in FIG. 1. An embodiment is shown in FIG. 1, which in addition to the image B and the orientation image OB, also shows a further display. This further display relates to a navigation image NB. In the navigation image NB which is shown in FIG. 1, the constant spacing between the images B, OB displayed can be seen in each case. All orientation images OB displayed here are spaced at a constant distance from image B.

The navigation image NB is intended as an overview image and the content displayed in the navigation image NB is orthogonal to the content which is displayed in the image B.

Usually the image B and the orientation images OB assigned to it involve individual, parallel slices of the volume dataset. The navigation image NB represents the volume dataset and additionally comprises an assignment to the image B/or to the orientation images OB. The navigation image NB can be a miniaturized display or a simplified representation of the volume dataset. The simplified representation can be calculated separately.

As can be seen from the figures, this assignment can be undertaken in the form of arrows which are displayed on the monitor M. In this case the arrows point from the image B and/or from orientation images OB to the respective assigned layer image in the navigation image NB. The arrows thus specify the spatial position of the image B and/or of the orientation images OB within the navigation image NB. Other embodiments of the invention provide other forms of assignment (and no arrows) such as colored outlines, colored markings, single dashes or lines or cross-hatching or other optical references.

Figure 2:
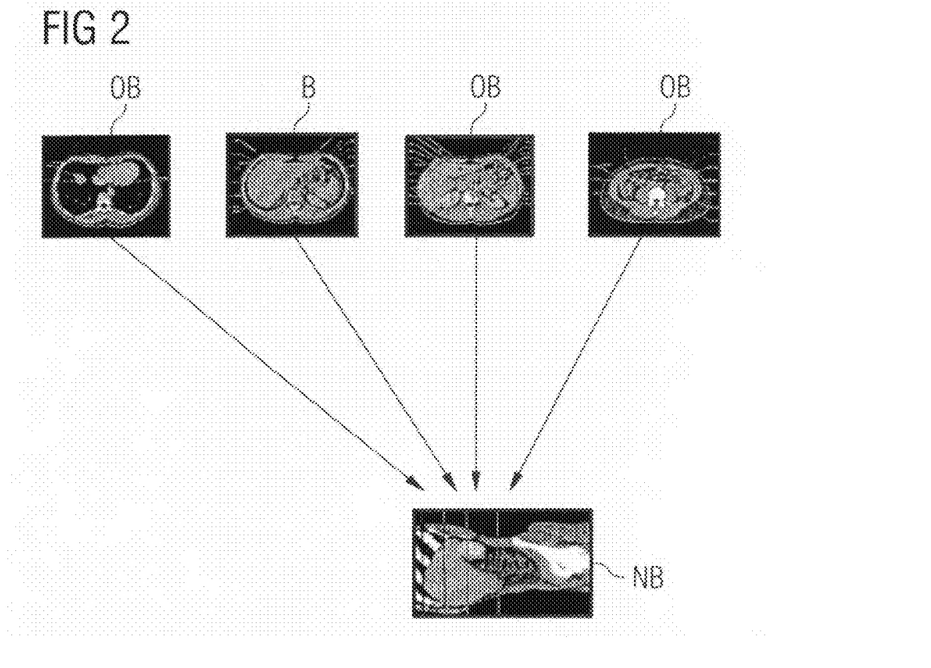
FIG. 2 shows an overview-type diagram of orientation images, based on an anatomy-related orientation measurement in accordance with an advantageous embodiment of the invention which refers to an example.

As shown in FIG. 2, the user can at any time very rapidly and simply obtain an overview of where and especially in which anatomic structure he is currently located and which anatomic structures are affected by the likewise displayed orientation images OB.

The display of the navigation image NB is however facultative and does not absolutely have to be displayed. It is also possible for the user to be able to initiate the display of the navigation image NB with a corresponding user interaction.

The display of the orientation images OB in addition to the image B can inventively be based on various models. The first model is the so-called distance-based model. This model will also be referred to in this application as a distance-based orientation measurement. The second model is an anatomy-based model. Within the framework of at least one embodiment of the invention this second model will be referred as an anatomy-related orientation measurement.

These two models will be explained in greater detail below. In alternate embodiments a combination of the models previously mentioned can also be used. In addition other models can also be employed which are based on a multidimensional display for example or which are aligned towards throughput speeds or other types of functional imaging. With the distance-related orientation measurement a distance is prespecified. This distance identifies how far the respective orientation images OB are to be from the current image to be displayed B. In other words the distance relates to the measure of distance between the image B and the orientation images OB assigned to it.

Precisely this distance, which is shown in the navigation image NB in FIGS. 1 to 4, is also reflected in the slices. In FIG. 1 this distance is constant. In other words, the image B and the orientation images OB each have a constant spacing. In the navigation image NB those sectional images for which an image B or an orientation image OB is displayed are shown highlighted. In FIGS. 1 and 2 the displayed sectional images are highlighted by highlighted identification of the respective sectional plane. Alternately other types of highlighting (e.g. color etc.) can be selected here. To make for an easier assignment between image B or orientation image OB respectively and their position within the navigation image NB, arrows are provided which point from the image B or from the respective orientation image OB to the sectional plane within the navigation image NB.

A significant feature of an embodiment of the present invention is to be seen in the fact that variable selection is possible as to which orientation images OB are to be displayed for the respective image B. The user can determine here in the individual case how many orientation images OB he would like to have displayed to him, at what size he would like to see said images and with what spacing or of which anatomic structures the orientation images OB are to be created.

Thus, depending on application, specific orientation images OB are selected from the volume dataset, so that they will be additionally displayed for the image B. The selection criteria can be varied in such cases. It is thus possible for example for the spacing—as shown in FIG. 1—to be constant.

As an alternative the spacing can be set with a constant growth factor, so that the orientation images will be displayed with an increasing spacing from image B. This is shown by way of example in FIG. 2.

In alternate embodiments, as well as the constant growth factor, another growth factor can also be set. In addition it is possible for the user to select the orientation images OB manually. This can be done for example by the user selecting a position within the navigation image NB. Then, on the basis of this selection the sectional image located there is displayed as a further orientation image OB. In the latter case the display of the navigation image NB is interactive, so that the user can select a position using a specific signal (e.g. a mouse click). This then automatically leads to the selected position leading to a choice of a sectional image of the volume dataset, and to this sectional image then being displayed as an orientation image OB.

By contrast with the distance-based orientation measurement described here, the anatomy-related orientation measurement can be employed as an alternative. With the anatomy-related orientation measurement anatomic structures can be automatically identified and selected in advance or selected by the user, as "target structures" so to speak.

Typically this can be done via a confirmation signal in response to an entry in a list displayed at the user interface. A set of anatomic features can be displayed in this list for example, from which the user can select all or a selection as relevant, e.g.: liver (upper part), liver (lower part), pancreas head, aorta etc.

Alternately the anatomic structures can be identified as relevant on the basis of the acquired metadata in an automated fashion in the header of the acquired image data. For example on the basis of the DICOM Attribute "Procedure Code" and/ or "Reason for Study". Accordingly images within the current image datasets, which have been acquired from the modality in this context, are provided on the basis of the anatomic model with anatomic codes for the relevant anatomic "target structures" (e.g. using the DICOM "Primary Anatomic Structure Sequence", which can contain one or more anatomic codes per image).

As an alternative or cumulatively thereto an expert system module can be used in order to assign the slices to an anatomic structure. In other words one or more structure(s) can initially be identified by the user (e.g. by setting a marking and assigning a code) or an automatic detection of at least one structure can be undertaken (e.g. by segmentation and/or known mechanisms for pattern recognition). On this basis other structures and the codes assigned to them will be provided automatically for the purposes of navigation based on the model in relation to these initially detected structures.

Within the framework of an embodiment of the present invention an anatomic model will be made available that takes account of the relationship between anatomic variables, which are dependent on height, weight, age, gender and further parameters of the respective patient. Statistical values are also included here, so that the anatomic model can include the following information:

"For a male patient of height x, weight y, age z, the pancreas head is on average, in relation to a y-axis through the body, w centimeters away from the kidney". The anatomic model is preferably stored in the database and can be applied via the suitable queries.

If the doctor has now identified specific anatomic structures in advance as relevant or if these are detected automatically on the basis of metadata of the examination performed, there is initially access to the anatomic model with the spatial relationships of the relevant anatomic structures. These structures will then be selected automatically in the volume dataset—as described above—by means of anatomic codes and displayed as orientation images OB. Preferably all the method steps given here occur automatically, i.e. without user interaction.

In the example depicted in FIG. 2 the image B relates to a pancreas head. The image B is shown in FIG. 2 in the third position. A number of orientation images OB is displayed for this image B. In FIG. 2 in the orientation images OB, seen from right to left, the upper part of the liver, the truncus coeliacus, the pancreas head and the aorta bifurcation are to be typically displayed. Both the image B and also the orientation images OB are provided with arrows which are designed to indicate their respective position within the navigation image NB. They refer to the respective sectional image that is represented highlighted in the navigation image NB (in FIGS. 1 and 2 by the lines running vertically within the navigation image NB.)

Figure 3:
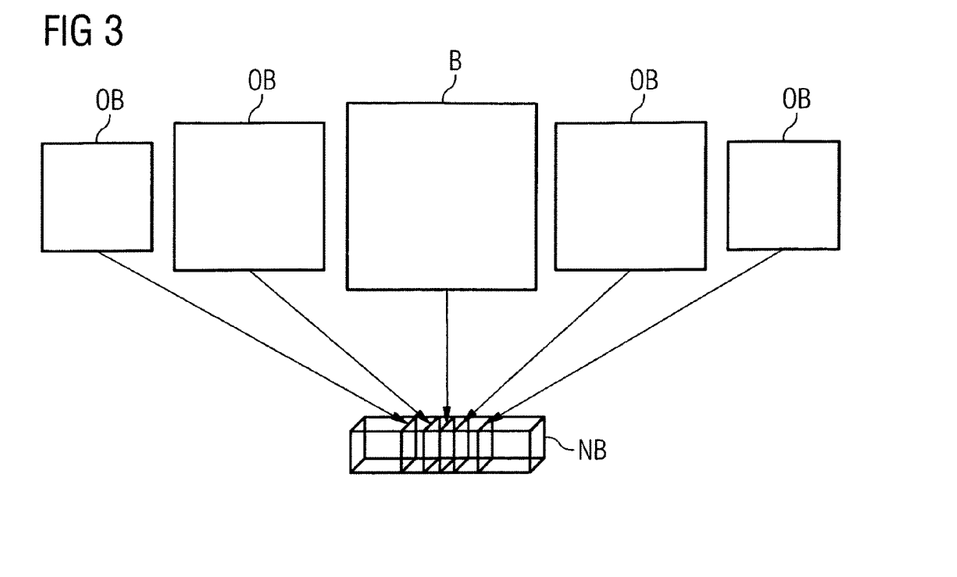
FIG. 3 shows a schematic diagram of an image, a number of orientation images with increasing spacing and a navigation image according to an example embodiment of the invention.

Shown in FIG. 3 is a schematic display of the image B, of the assigned orientation images OB and the navigation image NB, with the orientation images OB being selected with an increasing distance from image B. In the example in FIG. 3 the image B is shown as the largest image, while the orientation images OB are shown as being ever smaller the greater distance they are from image B. The advantage of this is that the most important images (in the vicinity of the focus of interest) are shown largest and the most unimportant image contents are shown smallest. Both the image B and also the orientation images OB again include references to their spatial position within the navigation image NB. As can be seen from FIG. 3, the distance between the orientation images OB becomes ever greater towards the outside. In the example depicted in FIG. 3 both the image B and also the orientation images OB are two-dimensional. Accordingly the references (arrows) point to individual slices within the volume dataset or within the navigation image NB.

In an alternate embodiment of the invention so-called multi planar reformatting is to be used as a basis for the display of the image B and/or of the orientation images OB. As an alternative to multi planar reformatting, other methods for generating three-dimensional views (which are subviews for the volume dataset so to speak) can also be used. In multi planar reformatting a number of slice datasets are merged and a mathematical superimposition of the respective slice datasets is computed in order to generate a three-dimensional slice stack of a specific thickness. The slice stack is able to be preset in accordance with a preferred embodiment of the present invention. In particular the slice thickness of image B can be set independently of the slice thickness of the orientation images OB.

Figure 4:
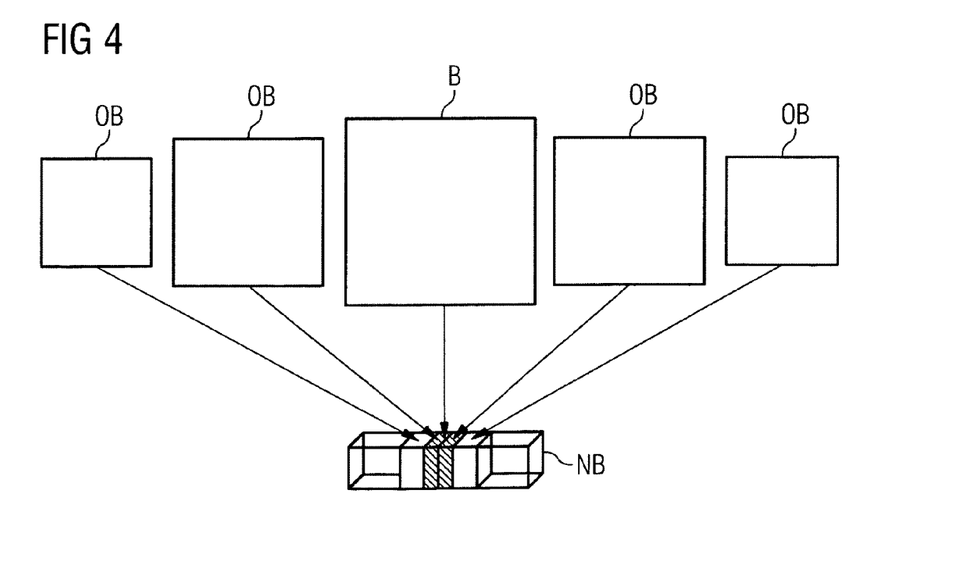
FIG. 4 shows a schematic diagram of an image, a number of orientation images and a navigation image for an MPR display with increasing scope in accordance with an advantageous embodiment of the present invention.

A typical display of image B and orientation images OB which are based on the multi planar reformatting described above is depicted schematically in FIG. 4. In this embodiment a setting can be made in advance as to whether the image and/or the orientation images OB are to be displayed as two-dimensional or three-dimensional. In this example a three-dimensional display of the image B has been selected. Independently of this it can likewise be selected whether the orientation images OB for the three-dimensional image B are to be displayed as three-dimensional or two-dimensional images. In the example shown in FIG. 4 the orientation images OB are also depicted as an image stack and thereby as three-dimensional images. Accordingly the arrows going out from the image B and the orientation images OB do not point to individual slice images but to blocks of slices. This is represented in FIG. 4 by the highlighted cubes or blocks within the navigation image NB.

All the modalities for display mentioned above can also be combined with one another. It is thus possible for example that in each of the previously mentioned embodiments the user also has the additional opportunity of selecting individual slices manually from the navigation image NB, so that these will then be displayed as an orientation image OB.

Navigation in the image stack (volume dataset) can be undertaken for example via scrolling, clicking on the adjacent images or on a desired position within the image stack.

With the interactive design of the navigation image NB it is possible to find relevant anatomic structures in a very efficient manner.

A major advantage of an embodiment of the inventive solution can be seen in the fact that the form of the navigation is user-specifically configurable. Thus the doctor can select for example whether he would rather navigate on the basis of physical distances or whether he requires an anatomy-based navigation. In addition a combination of distance-based and anatomy-based navigation is also possible.

Figure 5:
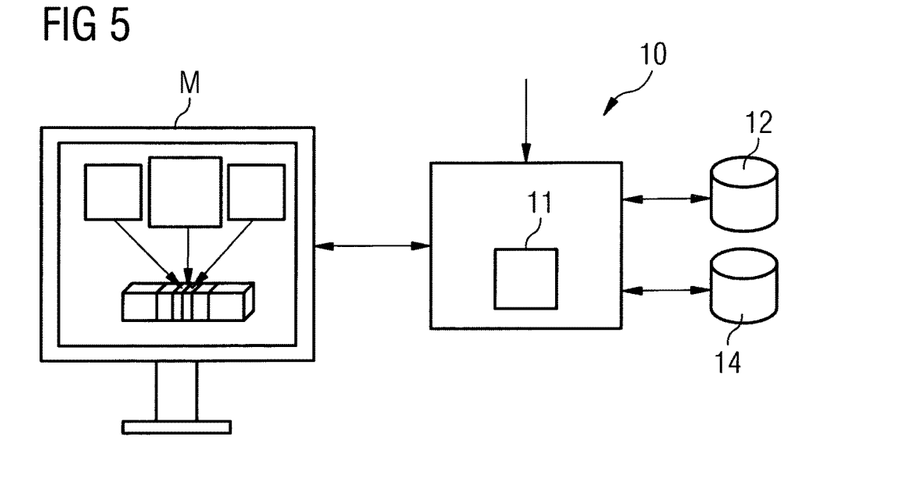
FIG. 5 shows an overview-type schematic diagram of individual modules of an inventive system, as can be employed in a further example embodiment.

FIG. 5 is designed to show a schematic diagram of a structure of an inventive system 10 in accordance with a preferred embodiment of the system. The system comprises a unit which comprises a monitor control module 11. The monitor control module 11 is used to control the display of slice datasets of a volume dataset on the monitor M of the computer-aided system. The unit into which the monitor control module 11 is integrated or the monitor control module 11 itself access metadata 12 and/or display parameters 14. The metadata 12 and the display parameters 14 can be stored in the same or in different databases. The metadata 12 typically involves information such as:

Gender of the patient age, size, previous illnesses, previous medical history, examination types (CT, MRT, US etc.), which had previously been carried out, a clinical problem in relation to the patient etc. The display parameters 14 relate to all parameters in relation to the display of the image B, of the orientation images OB and/or navigation image NB. The display parameters 14 can match or can be different for the image B, the orientation images OB and for the navigation image NB.

In particular settings can be made here for the size of the display, at the size of the window, the type of highlighting of the slice images in the navigation image NB, contrast defaults etc. In FIG. 5 the arrow which points to the unit from above which includes the monitor control module 11 is intended to indicate that there is also provision here for user inputs via a corresponding user interface, so that the user can make entries to control the system. These entries can for example relate to the display parameters 14.

In addition the user can make entries in respect of the orientation measurement to be selected. As shown in FIG. 5, the inventive monitor control module 11 can also be integrated into a more complex system 10 which is designed to be more comprehensive for example and is based on the computer-aided execution of a medical workflow.

Finally it should be pointed out that the description of the invention and the example embodiments are not to be understood as being basically restrictive in respect of a specific physical realization of the invention. For an appropriate person skilled in the art it is especially evident that the invention can be realized partly or completely in software and/or hardware and/or distributed between a number of physical products—especially also computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

B Image
OB Orientation image
NB Navigation image
M Monitor
10 System
11 Monitor control module
12 Metadata
14 Display parameters

What is claimed is:

1. A method for displaying at least one medical image from a volume dataset on a monitor of a computer-aided device with orientation images from the volume dataset, the volume data set containing a plurality of images including the medical image and a plurality of associated orientation images captured anatomically adjacent to the medical image, the method comprising:
   determining or providing an orientation measurement;
   applying the determined or provided orientation measurement to the volume dataset in order to select, from the volume dataset, orientation images which correspond to the determined or provided orientation measurement;
   displaying the at least one medical image together with the selected orientation images captured anatomically adjacent to the medical image; and
   displaying a navigation image, the navigation image being a single image representing an overview of the plurality of images in the volume data set viewed from a position orthogonal to the at least one medical image and including position markings identifying spatial positions of the displayed at least one medical image and the selected orientation images within the overview of the volume data set such that the position markings illustrate relative spatial positions of the plurality of images within the navigation image that is the single image representing the overview of the volume data set, wherein
      the navigation image is interactive such that different ones of the at least one medical image and associated orientation images within the volume dataset are automatically displayed by activating an associated area of the navigation image.

2. The method as claimed in claim 1, wherein the orientation measurement is selectable from a set which comprises:
   a distance-related orientation measurement identifying a distance between a respective orientation image and the at least one medical image; and
   an anatomy-related orientation measurement.

3. The method as claimed in claim 2, wherein a distance of the distance-based orientation measurement is constant or is able to be set to grow in accordance with a configurable growth parameter.

4. The method as claimed in claim 2, wherein the anatomy-related orientation measurement is based on an anatomic model provided, with all or selected images of the volume dataset being assigned an electronic anatomic code.

5. The method as claimed in claim 2, wherein the orientation measurement is determined automatically on the basis of metadata established for the volume dataset.

6. The method as claimed in claim 1, wherein the orientation measurement is determined automatically on the basis of metadata established for the volume dataset.

7. The method as claimed in claim 1, wherein the navigation image is two-dimensional or three-dimensional, and an anatomic structure is labeled and assigned to the navigation image.

8. The method as claimed in claim 1, wherein the displayed medical image and the displayed orientation images include a reference to their respective spatial position in the navigation image.

9. The method as claimed in claim 1, wherein the orientation images will be displayed automatically and almost at the same time as the medical image.

10. The method as claimed in claim 1, wherein at least one of the display of the orientation images and the display of the navigation image is initiated by a user interaction during or after the display of the medical image.

11. The method as claimed in claim 1, wherein display parameters for display of the at least one medical image, the orientation images and the navigation image are able to be configured.

12. The method as claimed in claim 1 wherein at least one of the medical image and the orientation images are three-dimensional image datasets with a preselectable slice thickness.

13. The method as claimed in claim 12, wherein the slice thickness of the medical image is selectable separately from the slice thickness of the orientation images.

14. A monitor control module for controlling display of at least one medical image from a volume dataset on a monitor of a computer-aided device with orientation images from the volume dataset, the volume data set containing a plurality of images including the medical image and a plurality of associated orientation images captured anatomically adjacent to the medical image, the monitor control module comprising:
   a determination module designed to determine or to provide an orientation measurement;
   a control module designed to apply the orientation measurement of the determination module to the volume dataset, in order to select, from the volume dataset, the orientation images that correspond to the orientation measurement determined or provided; and
   a display module configured to,
      display the medical image together with the selected orientation images captured anatomically adjacent to the medical image, and
      display a navigation image on the monitor, the navigation image being a single image representing an overview of the plurality of images in the volume data set viewed from a position orthogonal to the medical image and including position markings identifying spatial positions of the medical image and the selected orientation images within the overview of the volume data set such that the position markings illustrate relative spatial positions of the plurality of images within the navigation image that is the single image representing the overview of the volume data set, wherein
      the navigation image is interactive such that different medical images and associated orientation images within the volume dataset are automatically displayed by activating an associated area of the navigation image.

15. A system for displaying at least one image from a volume dataset, comprising:
   a monitor, intended for display of images and assigned orientation images; and
   a monitor control module as claimed in claim 14, the monitor control module including a data link to the monitor and able to include a user interface.

16. A computer program product loadable or loaded into a memory of a computer, including computer-readable commands for executing the method as claimed in claim 1 when the commands are executed on the computer.

17. A computer readable medium including program code segments for, when run on a computer, executing the method as claimed in claim 1.

* * * * *